United States Patent [19]

Morane et al.

[11] 4,093,124
[45] June 6, 1978

[54] ATOMIZER WITH AIR INLET VALVE

[75] Inventors: Bruno Morane, Paris; Yves Hardouin, Survilliers; Jean-Louis Gueret, Paris, all of France

[73] Assignee: L'Oreal, Paris, France

[21] Appl. No.: 759,657

[22] Filed: Jan. 17, 1977

Related U.S. Application Data

[63] Continuation-in-part of Ser. No. 708,367, Jul. 26, 1976, abandoned.

[30] Foreign Application Priority Data

Oct. 20, 1976 France .............................. 76 31523

[51] Int. Cl.² .............................................. B65D 1/32
[52] U.S. Cl. .................................... 239/327; 128/206; 222/189
[58] Field of Search ............... 239/327, 356, 362, 363, 239/575, 590; 222/189, 211, 212, 215; 128/206

[56] References Cited

U.S. PATENT DOCUMENTS

| | | | |
|---|---|---|---|
| 3,176,883 | 4/1965 | Davis, Jr. ........................ | 239/327 X |
| 3,333,741 | 8/1967 | Radcliffe .......................... | 222/189 |
| 3,358,883 | 12/1967 | Loe ................................... | 222/189 X |
| 3,519,208 | 7/1970 | Marchant ........................... | 239/327 |
| 3,679,137 | 7/1972 | Marchant ........................... | 239/327 |
| 3,760,987 | 9/1973 | Meterhoefer ..................... | 222/189 X |
| 3,794,247 | 2/1974 | Corsette ............................ | 239/327 |

*Primary Examiner*—Joseph F. Peters, Jr.
*Assistant Examiner*—Michael Mar
*Attorney, Agent, or Firm*—Brisebois & Kruger

[57] ABSTRACT

Atomizer for liquids is mounted on a compressible container for the liquid so as to define an atomizing chamber in the neck of the container, which has an outlet nozzle and is connected through a depending tube to the lower part of the container and through a short duct to its upper part. The container is also connected to the open air through inlets controlled by non-return valves preventing the escape of fluid therethrough. When the container is compressed liquid flows into the atomization chamber through the tube, and air flows into it through the duct, so that a spray is dispensed through the nozzle. When the container is permitted to expand air is sucked in through the air inlets, which are larger in section than the nozzle. In one embodiment filters are provided to filter air drawn in through the air inlets.

19 Claims, 7 Drawing Figures

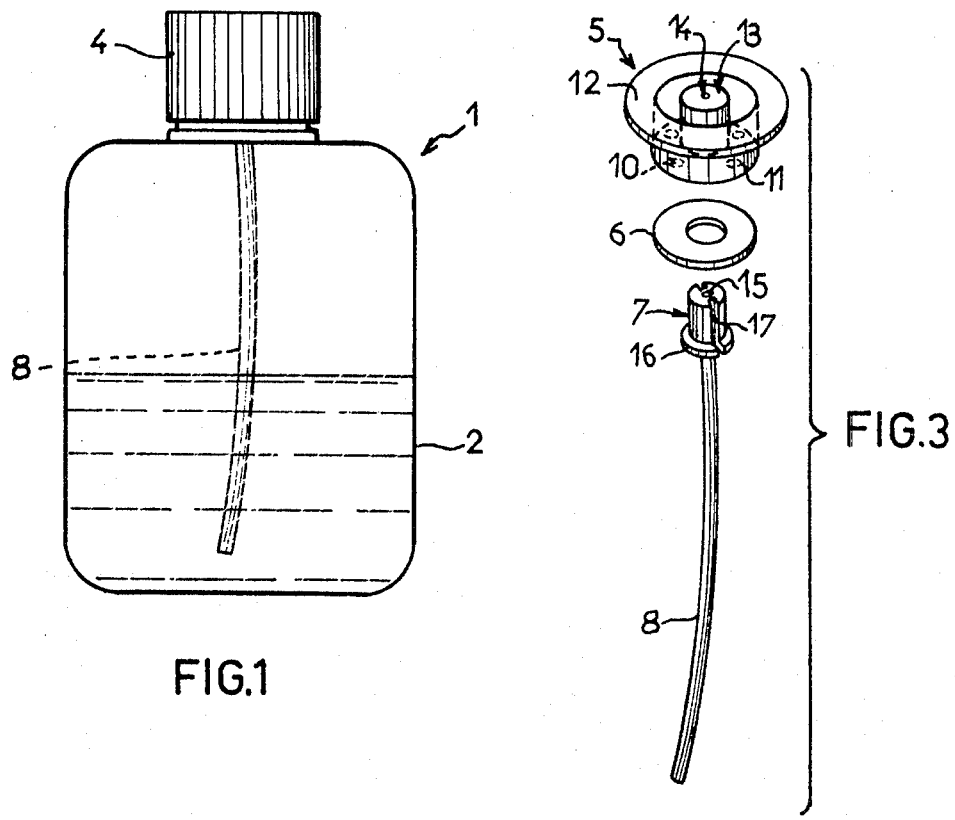
FIG.1
FIG.3
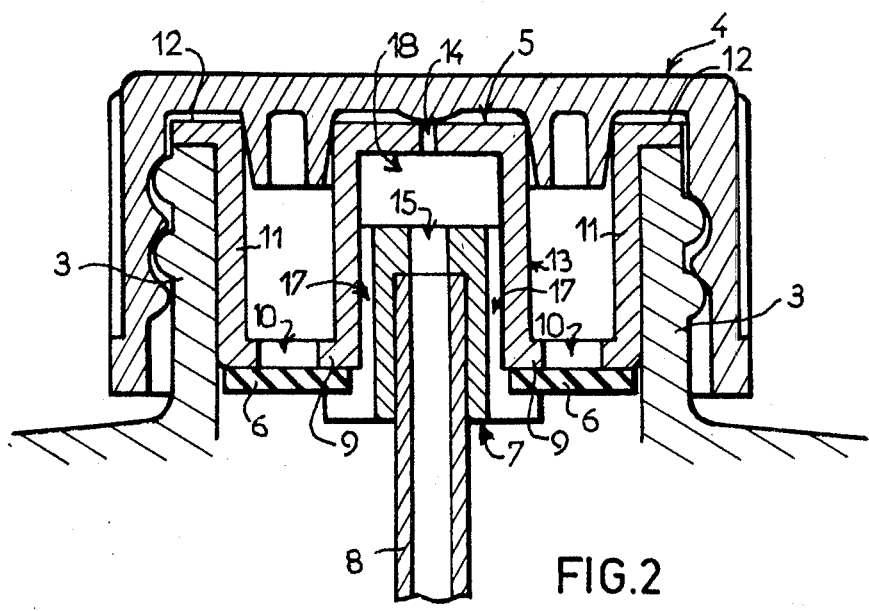
FIG.2

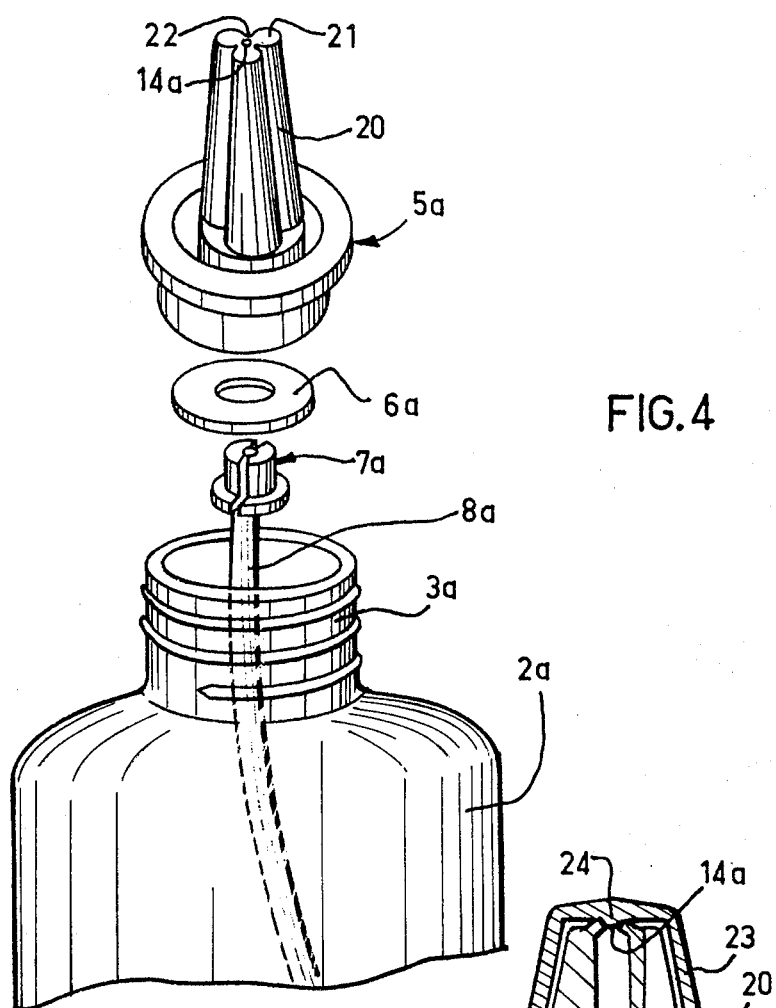
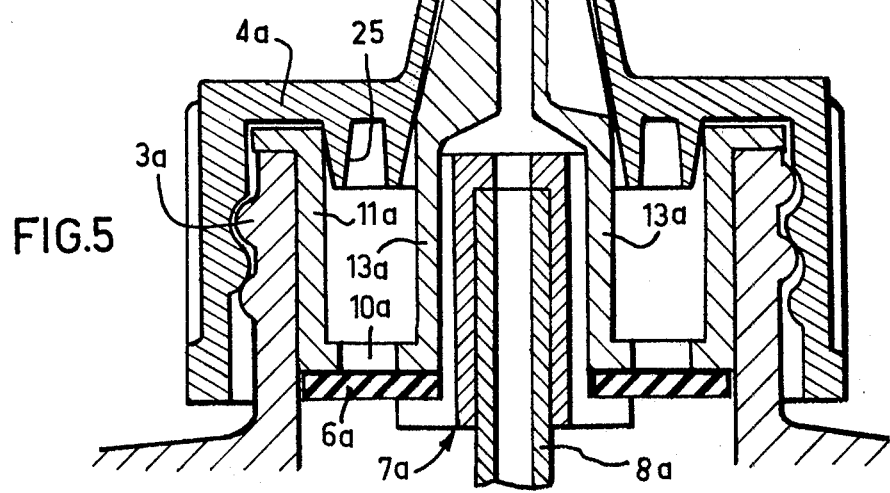

ATOMIZER WITH AIR INLET VALVE

This application is a continuation-in-part of our prior application Ser. No. 708,367 filed July 26, 1976 now abandoned.

SUMMARY OF THE INVENTION

In order to spray a liquid product, for example, so as to carry out a localized treatment of the skin or hair, it is conventional to utilize an atomizing container which the user actuates by pressure, deforming the flexible walls of the container to expel the product which is stored therein. This type of atomizer is most frequently equipped with a spray head mounted on the neck to which a depending tube is connected. This depending tube is adapted to direct the liquid product from the bottom of the container to a nozzle through which it is dispensed. While this method of storage and dispensing is particularly advantageous because of its simplicity and its low cost, there are certain inconveniences inherent in its structure.

In effect, this type of container is not, in general, capable of operation regardless of the position in which it is held by the user. In particular, when the container is positioned upside down, the depending tube is no longer in contact with the liquid product. Moreover, it is known that the product is dispensed by alternately compressing the flexible wall of the body of the container, so that each deformation produced by the user results in the atomization of a certain quantity of the product to be dispensed. However, between two successive atomization steps, it is necessary, after the user has released his pressure, to permit the container to return to its initial shape, that is to say to permit the passage of air into the container. Since this return of air takes place through a nozzle of small dimensions, it follows that the user, especially when using a large container, is obliged to wait for a relatively long time before being in a position to cause additional atomization. Moreover, the spray head may become contaminated in the course of use, for example, when brought in contact with the mucous tissues, and the return of air through the polluted nozzle may contaminate the liquid product remaining in the container.

The invention proposes to provide an atomizer of the general type described above which makes it possible to overcome the aforesaid disadvantages. The device according to the invention has, as compared with the storage methods of the prior art, the triple advantage of being practical, rapid in operation and clean. The atomizer proposed may be used in all positions. The waiting period between two successive dispensing actuations is reduced to a minimum by the addition of large air intake orifices adapted to be closed by a valve member and finally, the risk of pollution of the liquid to be dispensed is reduced because the intake of air does not occur through the ejection nozzle.

It is therefore an object of the present invention to provide, as a new article of manufacture, an atomizer for spraying a liquid product, for example a cosmetic or pharmaceutical product, said atomizer comprising a container having a spray head mounted on its neck, the walls of said container being flexible so that the user may deform them by pressure to expel the liquid product stored therein. A depending tube positioned inside the container cooperates with at least one ejection orifice formed in the spray head and is characterized by the fact that the depending tube opens into a spray chamber, the wall of which is provided with one or more ejection orifices. At least one duct opens into the spray chamber and places the neck of the container in communication with said chamber. The spray head is moreover pierced by at least one air intake orifice controlled by a valve member permitting the passage of outer air into the container when a depression is created inside the container after an atomization step produced by compressing the walls of said container.

In a preferred embodiment of the atomizer according to the invention, the air intake orifice or orifices has or have a total cross section greater than that of the ejection orifice. The air intake orifices are closer to the bottom of the container than the ejection orifice. The spray head is a member which is generally cylindrical in shape comprising an annular bottom, to the edge of which a peripheral mounting skirt is attached, which skirt is mounted inside the neck. A hollow shaft which is encircled by said skirt is also attached to said end. This shaft is closed at its upper end by a wall in which the ejection orifice or orifices is or are located. The mounting skirt is provided on its edge remote from the one which is connected to the annular bottom of the spray head with an annular shoulder projecting radially outward with respect to said skirt, which shoulder bears on the edge of the neck.

A plurality of air intake orifices are located in the bottom of the spray head, the axes of said orifices being preferably positioned at regular intervals concentrically with respect to the axis of the spray head. The depending tube opens into the atomizing chamber substantially on the axis of the ejection orifice. The depending tube is equipped with a tip seated inside the hollow shaft and defining the atomization chamber therewith. Longitudinal grooves are formed in the lateral peripheral wall of the tip and cooperate with the lateral inner wall of the passage to form ducts connecting the atomization chamber to the neck of the container. The grooved tip is a member discrete from the depending tube, which is generally cylindrical in shape and has an axial bore. The depending tube is fixed to the tip by forcing one of its ends into said bore. The grooved tip comprises, on its lateral cylindrical wall near the end through which the depending tube is inserted, a collar projecting radially with respect to said tip. Notches formed in this collar are radially aligned with the longitudinal grooves. The tip has two diametrically opposed grooves, each extending along one of the generatrices of the cylindrical lateral wall. The air intake orifices in the annular bottom of the spray head are adapted to be blocked by a flexible membrane acting as a valve member, the bearing surface of said membrane being constituted by the annular bottom surface on the inside of the container. The flexible membrane is a disc which is centered about the grooved tip and inserted between the collar on the tip and the corresponding surface of the annular bottom. On the lateral external wall of the neck are threads adapted to cooperate with threads formed on the inner lateral wall of a cap to insure sealing of the atomizing container.

It should be emphasized that most of the parts which constitute the atomizer proper, that is to say, the depending tube, the grooved tip, and the spray head, may be made in a simple manner, for example, by molding from plastic material. Their cost is consequently very low.

One of the advantages which the vaporizer exhibits during the course of use is that it may operate in any position in which it is placed by the user. Even when the container is positioned upside down the user may also atomize the product contained therein. The depending tube, which cannot then be supplied with liquid, serves to admit air from within the container into the atomization chamber while the ducts defined by the grooves of the tip and the wall of the passage permit the passage of liquid from the container into the atomization chamber where the air-water mixture may then be atomized.

When the user exerts pressure on the flexible walls of the container, it should be noted that the membrane which acts as a valve member is pressed against the air intake orifices, thus preventing the passage of air into the container through these orifices. When the user releases the pressure the container tends to return rapidly to its original shape because of the easy passage of air into the container through the air intake orifices, which are quite large. It is thus possible to initiate a new atomization within a very short time, which is not the case with the devices of the prior art in which the re-entry of air takes place through the spray nozzle which, by reason of its function, is necessarily of small dimensions.

Moreover, this arrangement makes it possible to reduce the risk of polluting the liquid stored in the container since the return of air does not take place through the ejection orifice of the spray head which is capable of coming into contact, with soiled surfaces, for example the mucous membranes of a sick person, when this type of atomizer is used to dispense liquid pharmaceutical products. Once, however, the user releases his pressure after expelling liquid from the container, the return of air into the container takes place through the air intake orifices, which are no longer blocked by the valve member because of the sub-atmospheric pressure created inside the container. It is thus clear that, between two successive sprayings, a return of air from the outside of the container takes place through the air inlet orifices and this air comes in contact with the liquid which is stored inside the container. This leads to the risk of contamination of the product to be atomized when the ambient air carries solid particles or germs, even though no air is drawn in through the ejection orifice itself.

In an embodiment designed to overcome this disadvantage the air intake orifices of an atomizer of the type already described are associated with at least one porous filter permitting the passage of air into the container, such filters being designed on the one hand to prevent the penetration into the container of solid particles and, on the other hand, to render the air entering the container aseptic because of the deposit of an appropriate bactericide on the filters. These porous filters have two particular characteristics, that of being made of a material which is not softened by the product to be sprayed and that of being treated with a bactericide which is both insoluble in the product to be sprayed and chemically inert with respect to the latter, in order to avoid any alteration in the case in which the air inlet valve lets a little liquid pass which could then come in contact with the porous filter.

Advantageously, the porous filter consists of an assembly of hydrophobic fibers forming a textile support which may be woven, non-woven, or knitted, and which is treated with an appropriate bactericide.

In a preferred embodiment the porous filter is made of a material which is not wetted by the product to be sprayed and which is stored in the container. The material of which the porous filter is made is treated with a bactericidal product. The bactericidal product is insoluble in the product to be sprayed and does not react therewith. The porous filter is made of hydrophobic fibers preferably selected from the group consisting of polyvinyl chloride, polyamine, polyester, polypropylene, and polyacrylic fibers. The porous filter consists of a woven, knitted, or non-woven textile support and is in the form of a disk positioned in alignment with the inlet orifice or orifices between the outside of the container and the valve member, said disk being inserted between the peripheral skirt and the central shaft of the spray head. The porous filter bears along its two peripheral edges on two annular shoulders positioned between the peripheral skirt and the central shaft of the spray head, one of the shoulders being formed on the inner wall of said peripheral skirt while the other is formed on the outer wall of the central shaft. The porous filter is held against the two annular shoulders on which they rest by means of a perforated retaining ring which is adapted to be applied to the porous filter. This ring is inserted between the porous filter and an annular ridge provided in relief on the inner wall of the peripheral skirt of the spray head. The peripheral skirt is provided on its upper edge with an annular flange projecting radially from the skirt. This shoulder rests on the edge of the neck. The porous filter is, after mounting, positioned substantially perpendicular to the axis of the spray head between the bottom in which the air intake orifices are pierced and the said annular flange. The wall which closes the upper part of the hollow central shaft of the spray head constitutes a conical or frusto-conical spout at the smaller end of which the ejection orifice or orifices is formed.

In the embodiment illustrated in FIGS. 6 and 7, the inlet orifices are protected from any external contact at the moment at which the atomizer is operated, since they open into an annular space between the peripheral skirt and the central hollow shaft of the spray head and are also located with respect to the body of the container, at a level beneath that of the ejection orifice. The air which penetrates into the container through the air inlet orifices is not capable of contaminating the liquid to be sprayed since it passes through a porous filter treated with a bactericide which renders it substantially aseptic.

In particular, the atomizer according to the invention may be used to dispense nasal sprays of pharmaceutical liquids. In this case the upper part of the central passage is shaped to penetrate the nasal passages where the mists are to be used. In such a case, the upper part of the hollow shaft of the spray head has a conical or frusto-conical tip, the smaller end of which contains an ejection orifice.

In order that the object of the invention may be better understood, a preferred embodiment of the invention will now be described, purely by way of illustration and example, with reference to the accompanying drawings, on which:

FIG. 1 is an elevational view of one embodiment of an atomizing container according to the invention;

FIG. 2 is an axial sectional view on a larger scale taken through the spray head mounted on the neck of the container shown in FIG. 1;

FIG. 3 is an exploded view showing the different components of the atomizing device of FIG. 2;

FIG. 4 is an exploded view showing the different components of an atomizing device adapted to dispense nasal mists;

FIG. 5 is an axial sectional view taken through the atomizing device of FIG. 4;

Figure 7:
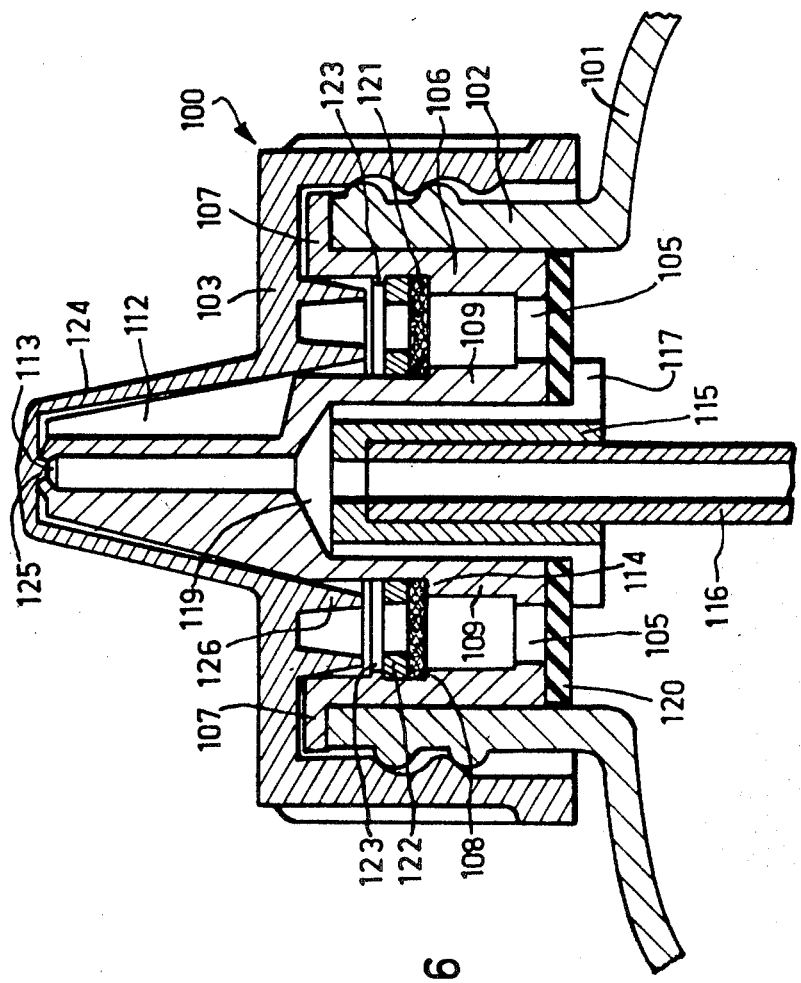
FIG. 7 is an axial sectional view taken through the embodiment of FIG. 6.

Referring now to FIGS. 1 to 3, it will be seen that reference numeral 1 indicates an atomizer according to the invention, considered as a whole. The atomizer 1 consists of a container 2 made of a plastic material, which is sufficiently flexible to permit the user to easily deform its walls in order to eject the liquid product stored therein. The container 2 is provided with a neck 3 which is substantially cylindrical and the outer lateral wall of which is threaded. These threads are adapted to cooperate with threads formed on the inner lateral wall of a cap which closes the atomizer 1 during transportation or storage.

The atomizing device with which the container 2 is equipped consists of an assembly comprising four separate parts: a spray head 5, a washer 6 serving as a valve member, a grooved tip 7, and a depending tube 8.

The spray head indicated by reference numeral 5 is a member which is generally cylindrical in shape and fits into the neck 3 of the container. The head 5 comprises an annular bottom 9 pierced by four air intake orifices 10. These orifices 10 are circular and positioned at regular intervals concentrically with respect to the axis of the head 5.

A mounting skirt 11 is connected at right angles to the peripheral edge of the bottom 9. At the upper edge of the mounting skirt 11, which is remote from the one to which the bottom 9 is connected, there is an annular flange 12 extending radially with respect to the skirt 11. To the inner edge of the annular bottom 9 is connected to hollow shaft 13, which is cylindrical in shape, open at the end connected to the bottom 9 and closed at its top by a wall axially pierced by an ejection orifice 14.

The spray head 5 is attached to the container 2 by forcing the skirt 11 into the neck 3 until the annular shoulder 12 comes to bear against the edge of said neck. It will be observed that the air intake orifices 10 are located, with respect to the body of the container, at a level below that of the ejection orifice 14. It follows that the orifices 10 are protected from any outer contact when the atomizer is used.

The grooved tip 7 serves to connect the depending tube 8 to the spray head 5 which has just been described. This tip consists of a member molded from plastic material, which is generally cylindrical in shape, and has a bore 15 extending along its axis. Inside this bore is seated one end of the tube 8. Near the end through which the tube 8 enters, the grooved tip has an annular collar 16 perpendicular to the axis of said tip. This collar has an outer diameter greater than the inner diameter of the nipple 13. On the cylindrical outer wall of the tip 7 and along two of its generatrices are two grooves 17 which are diametrically opposite each other. The two channels 17 intersect, at the level of the collar 16, two notches formed in said collar. The grooved tip 7 fits into the nipple 13 and defines therewith an atomization chamber 18.

The atomization chamber 18 communicates with the outer air through the ejection orifice 14 and with the space within the container both through the bore 15 connected to the depending tube 8 and the two channels 17. The grooves 17 cooperate with the internal wall of the nipple 13 to define two ducts which connect the space within the container to the atomization chamber 18. The valve member adapted to block the air inlet orifices 10 in the annular bottom of the spray head 5 consists of a washer 6 made of rubber or any suitable flexible material. The washer 6 serves to permit the passage of air into the container after a dispensing step, that is to say once the pressure within the container falls below atmospheric pressure, and to prevent air within the container from escaping through the orifices 10 during the atomization step. This washer 6 is centered around the grooved tip 7 and gripped between the collar 16 and the corresponding surface on the annular bottom 9 of the spray head.

FIG. 3 shows how the atomization device which fits on the neck 3 of the container is assembled. The tube 8 is positioned in the bore 15 of the grooved tip. The washer 6 is threaded on to the grooved tip and is retained thereon by the collar 16. The grooved tip thus equipped is attached to the head 5 by forcing it into the nipple 13. In this position the washer 6 bears against the bottom 9 of the head 5. The atomization device thus assembled is fitted onto the neck 3 of the container, which has previously been filled with a liquid product to be atomized.

In order to carry out a dispensing step the user presses the walls of the container so as to eject the liquid product through the orifice 14, the depending tube 8 and the chamber 18. Simultaneously the air inside the container which cannot escape through the air intake orifices 10 which the valve member 6 blocks, enters the chamber 18 through the ducts 17 and is then ejected with the liquid product. Once the user relaxes his pressure, air re-enters the chamber through the orifices 10 which are no longer blocked by the valve member 6 because of the subatmospheric pressure inside the container. Since this return of air takes place very rapidly because the orifices 10 are quite large, the user is in a position to carry out a new atomization step after a very short time.

When the chamber is upside down atomization follows an inverse process. The ducts 17 lead the liquid product from the container to the chamber 18 while the depending tube, which is not supplied with the liquid product, passes air from the container into the chamber 18, the mixture of liquid and air in said chamber being then atomized by the orifice 14.

It should be emphasized that, despite the advantages resulting from the atomizer according to the invention, its construction is especially simple and its cost substantially the same as that of the most closely similar devices heretofore known.

Referring now to FIGS. 4 and 5, it will be seen that these show a device according to the invention quite similar to the one illustrated in FIGS. 1 to 3, said device being adapted to the distribution of nasal mists. By reason of the analogy of construction between this embodiment and the embodiment previously described, the description will not be repeated in detail and all the members corresponding to those in the embodiment of FIGS. 1 to 3 have been given the same reference numerals followed by the letter a.

The central nipple 13a of the dispensing head has a section having a frusto-conical surface 20. The conical surface 20 has a tri-lobular section 21 separated by grooves 22. The smaller end of the frusto-conical section has a dispensing orifice 14a. The cap 4a which covers the dispensing head 5a has, near its center, a frusto-conical seat 23 which fits onto the conical part 20 of the dispensing head 5a. The interior of the seat 23 has at the end of the conical section a protuberance 24 which, when the cap 4a is screwed onto the neck 3a of the container 2a, enters into the ejection orifice 14a to insure close sealing. In the same way the cap 4a carries an annular ring having lips 25 inserted between the skirt 11a and the central nipple 13a of the dispensing head 5a to insure a seal in case the valve member consisting of the washer 6a permits a small amount of the liquid within the container to leak by. It will be appreciated that this embodiment of the device according to the invention makes it possible to produce a nasal mist dispenser which is portable and to avoid any entrance of contaminated products into the container when the conical tip 20 is placed in a nasal passage of the user.

Figure 6:
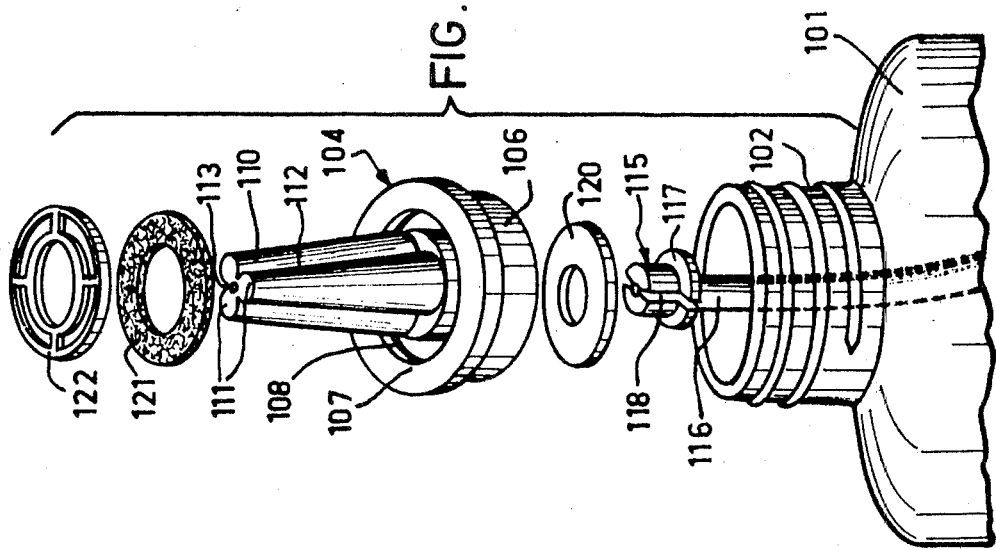
FIG. 6 is an exploded view of a second embodiment including a filter for air admitted through the air inlets.

Referring now to FIGS. 6 and 7, it will be seen that reference numeral 100 indicates an atomizer according to the invention adapted to the distribution of nasal sprays. This atomizer comprises a container 101 made of a plastic material which is sufficiently flexible to permit the user to easily deform its walls in order to eject the liquid product which is stored therein. The container 101 is provided with a neck 102 which is substantially cylindrical, the outer lateral wall of which carries threads. These threads are designed to cooperate with corresponding threads formed on the inner lateral wall of a cap 103 which closes the atomizer 100 during its transportation or storage.

Inside the neck 102 of the container 101 is a spray head 104. The head 104 comprises an annular bottom pierced by four air inlet orifices 105. These orifices 105 are circular and positioned at regular intervals concentrically with respect to the axis of the head 104. A substantially cylindrical mounting skirt 106 is connected to the peripheral edge of the annular bottom. At the upper edge of the skirt 106 which is remote from the one connected to said annular bottom is an annular flange 107 extending radially outward from the skirt 106. On the inner wall of the skirt 106 which is remote from the one which comes in contact with the neck 102 is an annular shoulder 108.

A hollow shaft 109 is connected to the inner edge of the bottom of the head 104 in which the air inlet orifices 105 are formed, and this shaft extends axially with respect to the skirt 106. The part of the central shaft 109 which is positioned inside the skirt 106 is cylindrical and is surmounted by a frusto-conical spout 110. The frusto-conical spout 110 has a section 111 having three lobes separated by grooves 112. The central shaft is open adjacent the annular bottom and closed at its upper part near the smaller end of the frusto-conical spout 110 by a wall pierced along the shaft axis by an ejection orifice 113. Opposite the annular shoulder 108 formed on the skirt 106 of the head 104 another annular shoulder 114 is formed on the external wall of the central shaft 109 and has substantially the same dimensions as the shoulder 108.

The spray head 104 is mounted on the container 101 by forcibly engaging the skirt 106 in the neck 102 until the flange 107 comes to bear against the edge of the neck.

A pierced tip 115 serves to connect a depending tube 116 to the spray head 104 which has just been described. This tip 115 consists of a member moulded from plastic material, generally cylindrical in shape, the axis of which is pierced by a bore. Inside this bore one end of the tube 116 is engaged. Near the end through which the tube 116 penetrates the pierced tip 115 is provided with a collar 117 extending perpendicularly to the axis of said tip, said collar having an outer diameter greater than the inner diameter of the shaft 109, measured in the vicinity of the bottom through which the orifices 105 are pierced. On the lateral cylindrical wall of the wall of the tip 115 and along two of its generatrices are formed two grooves 118 which are diametrically opposed. The two grooves 118 extend through the collar 117, thus forming two notches in the collar. The pierced tip 115 is adjusted inside the central hollow shaft 109 and defines therewith a spray chamber 119. The chamber 119 communicates both with the outer air through the ejection orifice 113 and with the space within the container, on the one hand through the depending tube 116 and, on the other hand, through the two grooves 118. The grooves 118 are positioned opposite the cylindrical inner wall of the hollow shaft 109 in order to define two ducts which connect the space within the container to that within the chamber 119.

A flexible ring 120 serves as the valve member for the air inlet orifices 105 which are pierced in the annular bottom of the spray head 104. The valve member 120 serves, on the one hand, to permit the passage of air into the container after a spraying step, that is to say when a sub-atmospheric pressure prevails inside the container, and, on the other hand, to prevent air within the container from escaping through the orifices 105 during the spraying step. This valve member 120 is, on the one hand, centered around the grooved tip 115 and, on the other hand, inserted between the collar 117 and the corresponding zone of the wall of the annular bottom of the spray head 104.

In order to prevent the air which penetrates into the container through the orifices 105 between two successive sprayings from contaminating the liquid to be sprayed, a porous filter 121 is provided. This filter serves to block the entrance to said orifices. The filter 121 is made of an assembly of fibers which are not wetted by the product to be sprayed and which is stored in the container. When the liquid product to be sprayed is an aqueous solution or a suspension in an aqueous medium, the fibers of the filter may advantageously be made of a hydrophobic material. Among the hydrophobic fibers which are suitable are polyvinyl chloride, polyester, polypropylene, polyamide, and polyacrylic fibers. The said hydrophobic fibers may be assembled to form a textile support which may be formed in any manner, whether woven or non-woven. The weight of the fibrous filter 121 used in this embodiment lies between 150 and 250 g/m$^2$.

The porous filter 121 serves as a filter for the air penetrating into the container since it removes therefrom solid particles found therein. But this filter also serves to destroy germs contained in the air penetrating into the container by treating them with an appropriate bactericide. The valve member 120 is capable of passing a small amount of the liquid to be vaporized which then comes in contact with the filter 121. This is why it is advantageous that the bactericide used be both insoluble in the liquid to be sprayed and chemically inert with respect thereto. In this example, the bactericide used is known under the trademark IRGASAN DP 300. The treatment of the filter 121 with such a bactericide may be carried out in a conventional manner, for example, by fulling. The porous filter 121 is in the form of a ring adapted to be threaded around the central shaft 109 to bear by its two peripheral edges on the two shoulders 108 and 109 provided for this purpose. On the porous filter 121 positioned above the air intake orifices 105 between the skirt 106 and the central sleeve 109 of the head 104 is retaining ring 122. The inner and outer diameters of the ring 122 are substantially identical to those of the porous filter 121. The retaining ring 122 consists of two concentric rings connected by four cross bars. In order to hold the retaining ring 122 against the porous filter 121 resting on the two annular shoulders 108 and 114 a thin peripheral snap fastening rib 123 is provided on the inner wall of the skirt 106 above the annular shoulder 108. The retaining ring 122 is introduced forcibly above the fibrous filter so as to be inserted between the filter 121 and the rib 123.

FIG. 6 shows the method of assembling the atomizer according to the invention which is mounted on the neck 102 of the container. Tube 116 is positioned in the inner bore of the grooved tip 115. The washer 120 is threaded onto the grooved tip and is retained thereon by collar 117. The grooved tip thus equipped is fastened to the head 104 by pressing it into the shaft 109. In this position the washer 120 bears substantially against the annular bottom of the head 104. The atomizer thus assembled is mounted on the neck 102 of a container which has previously been filled with the liquid product to be atomized. Once this operation has been carried out, the porous filter 121 and its associated retaining ring 122 are put in place as indicated.

The cap 103 which covers the spray head 104 during the transport or storage of the atomizer comprises, in its central zone, a frusto-conical part 124 which fits onto the frusto-conical part 110 of the head 104. The interior of the cap tip 124 comprises, at the end of the frusto-conical part a protuberance 125 which, when the cap 103 is screwed onto the neck 102 of the container 101, enters into the ejection orifice 113 to insure a fluid-tight seal. In the same manner, the plug 103 carries internally an annular ring having lips 126 which are inserted between the central shaft 109 and the skirt 106 of the spray head 104 to insure sealing when the valve 120 and the filter 121 permit a little of the liquid contained in the container 101 to pass therethrough.

In order to utilize the atomizer 100 adapted to the dispensing of nasal sprays, the user, after having unscrewed the cap 103, compresses the flexible walls of the container so as to cause the liquid to pass through the tube 116, the spray chamber 118, and be ejected through the orifice 113. Simultaneously, the air contained in the container, which cannot escape through the orifices 105 blocked by the valve member 120, passes into the chamber 119 through the two ducts 118 to be mixed and ejected with the liquid product. Once the user releases his pressure, the return of air into the container takes place through the fibrous filter 121 and the orifices 105 which are no longer blocked by the valve member 120. In this embodiment the upper part of the central shaft, to wit, the conical part 110, is positioned in the nasal passages in which atomization should take place. In such a case it is possible that the ejection orifice 113 may be soiled in the course of use since it comes into contact with the mucous membranes. However, the risk of pollution is reduced because the return of air does not take place through the ejection orifice 113, but through the air inlet orifices 105 which are blocked by the porous filter 121 treated by a bactericide. It is thus found that this nasal sprayer makes it possible to avoid contamination of the liquid contained in the container even when the conical spout 110 is positioned in a nostril of the user.

It will, or course, be appreciated that the embodiments which have just been described have been given purely by way of illustration and example, and may be modified as to detail without thereby departing from the basic principles of the invention.

What is claimed is:

1. In an atomizer for spraying a liquid product, said atomizer comprising a container having flexible walls and a neck, a spray head mounted on said neck, an atomization chamber inside said spray head, a depending tube inside said container opening into said atomization chamber, at least one valveless ejection orifice leading from said chamber to the exterior of said container, and at least one duct connecting the spray chamber to the interior of the container so that the liquid product can be sprayed in atomized form both in an upright and an inverted position of the container, said spray head comprising an annular bottom the edges of which are connected to a peripheral mounting skirt fitted inside said neck and a hollow central shaft encircled by the mounting skirt, said hollow shaft being closed at its upper end by a wall pierced by said at least one ejection orifice, at least one air intake orifice in the annular bottom of the spray head cooperating with a valve member, the improvement according to which the depending tube terminates in a tip seated inside the hollow central shaft and cooperating with said spray head to define said atomization chamber, and the valve member is a flexible washer which covers said at least one air intake orifice when urged thereagainst by pressure within said container, said washer being centered around said tip and gripped between a collar formed on said tip and the corresponding area on the inner surface of said annular bottom.

2. Atomizer as claimed in claim 1 in which said at least one air intake orifice has a cross-section greater than that of said at least one ejection orifice.

3. Atomizer as claimed in claim 1 in which the end of the peripheral mounting skirt remote from the one to which the annular bottom of the spray head is connected is provided with an annular flange projecting radially outward from said skirt and which rests on the edge of the neck.

4. Atomizer as claimed in claim 1 in which a plurality of air inlet orifices are formed in the annular bottom of the spray head, the axes of said orifices being preferably positioned concentrically with respect to the axis of the spray head.

5. Atomizer as claimed in claim 1 in which the depending tube opens into the atomizing chamber substantially along the axis of the ejection orifice.

6. Atomizer as claimed in claim 1 in which the tip attached to the depending tube comprises grooves in its lateral wall which cooperate with the lateral inner wall of the hollow shaft to define the ducts which connect the spray chamber to the interior of the container.

7. Atomizer as claimed in claim 1 in which the tip is a member discrete from the depending tube, having a generally cylindrical shape and pierced by an axial bore, said depending tube having one end inserted into said bore.

8. Atomizer as claimed in claim 6 in which the tip has two diametrically opposed ducts extending along the generatrices of its lateral cylindrical wall.

9. Atomizer as claimed in claim 1 in which a collar is formed on the peripheral lateral wall of the tip and near the end thereof connected to the depending tube, said collar projecting radially outward from said tip and having notches formed therein intersecting said duct.

10. Atomizer as claimed in claim 1 adapted to distribute nasal mists in which the upper part of the central shaft of the spray head is closed by a conical or frustoconical spout defining said ejection orifice at its smaller end.

11. Atomizer as claimed in claim 1 comprising at least one porous filter positioned between said valve member and the outside of said atomizer in the path of air entering said container through said at least one air inlet orifice.

12. In an atomizer for spraying a liquid product, said atomizer comprising a container having flexible walls and a neck, a spray head mounted on said neck, an atomization chamber inside said spray head, a depending tube inside said container opening into said atomization chamber, at least one ejection orifice leading from said chamber to the exterior of said container, at least one duct connecting the spray chamber to the interior of the container, said spray head comprising an annular bottom the edges of which are connected to a peripheral mounting skirt fitted inside said neck and a hollow central shaft encircled by the mounting skirt, said hollow shaft being closed at its upper end by a wall pierced by said at least one ejection orifice, and at least one air intake orifice in the annular bottom of the spray head cooperating with a valve member, the improvement which comprises at least one porous filter positioned between said valve member and the outside of said atomizer in the path of air entering said container through said at least one air inlet orifice, in which the porous filter is made of a material which is not wetted by the product stored in the container and, in which the material of which the filter is made is treated with a bactericidal product which is insoluble in the product to be atomized and does not react therewith.

13. Atomizer as claimed in claim 12 in which the porous filter consists of hydrophobic fibers selected from the group consisting of polyvinyl chloride, polyamide, polyester, polypropylene, and polyacrylic fibers.

14. Atomizer as claimed in claim 12 in which the porous filter is in the form of a ring positioned in alignment with the air intake orifices outwardly of the container with respect to the valve member, said ring being inserted between the peripheral skirt and the central shaft of the spray head.

15. Atomizer as claimed in claim 14 in which the porous filter bears at its two pheripheral edges on two annular shoulders extending into the space between the peripheral mounting skirt and the central shaft of the spray head, one of the said shoulders being formed on the inner wall of said peripheral skirt while the other is formed on the outer wall of the central shaft.

16. Atomizer as claimed in claim 15 in which the filter is held on the two annular shoulders against which it bears by means of a perforated retaining ring positioned between said filter and an annular ridge formed in relief on the inner wall of the peripheral skirt of the spray head.

17. Atomizer as claimed in claim 12 in which the peripheral skirt of the spray head is provided with an annular flange on its upper edge remote from that at which it is connected to the bottom of said head, said flange projecting radially with respect to said skirt and bearing on the edge of the neck.

18. Atomizer as claimed in claim 17 in which the porous filter is positioned substantially perpendicularly to the axis of the spray head between the bottom in which the air inlet orifices are pierced and said annular flange.

19. Atomizer as claimed in claim 12 adapted to distribute nasal sprays, in which the wall which forms the upper part of the central shaft of the spray head constitutes a conical or frusto-conical spout having at least one ejection orifice at its narrow end.

* * * * *